(12) United States Patent
Ou et al.

(10) Patent No.: US 11,559,610 B2
(45) Date of Patent: *Jan. 24, 2023

(54) LOW TEMPERATURE CURED SILICONE LUBRICIOUS COATINGS

(71) Applicant: Ethicon, Inc., Somerville, NJ (US)

(72) Inventors: Duan Li Ou, Warren, NJ (US); Christophe Vailhe, Hillborough, NJ (US); Frank R. Cichocki, Easton, PA (US)

(73) Assignee: Ethicon, Inc., Raritan, NJ (US)

( * ) Notice: Subject to any disclaimer, the term of this patent is extended or adjusted under 35 U.S.C. 154(b) by 354 days.

This patent is subject to a terminal disclaimer.

(21) Appl. No.: 16/697,222

(22) Filed: Nov. 27, 2019

(65) Prior Publication Data
US 2020/0171198 A1  Jun. 4, 2020

Related U.S. Application Data

(60) Provisional application No. 62/773,102, filed on Nov. 29, 2018.

(51) Int. Cl.
*A61L 27/54* (2006.01)
*A61L 2/03* (2006.01)
(Continued)

(52) U.S. Cl.
CPC ............ *A61L 27/54* (2013.01); *A61L 2/03* (2013.01); *A61L 2/07* (2013.01); *A61L 2/20* (2013.01); *A61L 2/26* (2013.01); *A61L 17/005* (2013.01); *A61L 17/145* (2013.01); *A61L 31/10* (2013.01); *A61L 31/14* (2013.01); *A61L 31/16* (2013.01); *B05B 7/1606* (2013.01); *B05B 7/1686* (2013.01); *B05B 12/081* (2013.01); *B05B 15/00* (2013.01); *B05B 17/0615* (2013.01);
(Continued)

(58) Field of Classification Search
None
See application file for complete search history.

(56) References Cited

U.S. PATENT DOCUMENTS 2,941,696 A    6/1960  Edwin
3,187,752 A *  6/1965  Glick ............... A61L 17/145
                                              606/231
(Continued)

FOREIGN PATENT DOCUMENTS

CN    104531056 A    4/2015
CN    105586001 A    5/2016
(Continued)

OTHER PUBLICATIONS

Google scholar keyword search (Year: 2021).
(Continued)

*Primary Examiner* — Peter A Salamon

(57) ABSTRACT

Novel, lubricious coatings for medical devices are disclosed. The coatings provide improved lubricity and durability and are readily applied in coating processes a low temperatures that do not deform the device. The present invention is also directed to a novel platinum catalyst for use in such coatings. The catalyst provides for rapid curing, while inhibiting cross-linking at ambient temperatures, thereby improving the production pot life of the coatings.

15 Claims, 1 Drawing Sheet

(51) Int. Cl.

| | | |
|---|---|---|
| *A61L 2/07* | (2006.01) | |
| *A61L 2/20* | (2006.01) | |
| *A61L 2/26* | (2006.01) | |
| *A61L 17/00* | (2006.01) | |
| *B05B 7/16* | (2006.01) | |
| *B05B 15/00* | (2018.01) | |
| *A61L 17/14* | (2006.01) | |
| *C09D 7/20* | (2018.01) | |
| *C09D 7/62* | (2018.01) | |
| *A61L 31/10* | (2006.01) | |
| *A61L 31/14* | (2006.01) | |
| *A61L 31/16* | (2006.01) | |
| *C09D 5/14* | (2006.01) | |
| *C09D 183/04* | (2006.01) | |
| *C10M 107/50* | (2006.01) | |
| *B05B 12/08* | (2006.01) | |
| *B05B 17/06* | (2006.01) | |
| *B05D 1/02* | (2006.01) | |
| *B05D 3/04* | (2006.01) | |
| *C10N 40/00* | (2006.01) | |
| *C10N 30/16* | (2006.01) | |
| *C10N 50/08* | (2006.01) | |
| *A61M 11/00* | (2006.01) | |

(52) U.S. Cl.
CPC ............. *B05D 1/02* (2013.01); *B05D 3/0493* (2013.01); *C09D 5/14* (2013.01); *C09D 7/20* (2018.01); *C09D 7/62* (2018.01); *C09D 183/04* (2013.01); *C10M 107/50* (2013.01); *A61L 2202/181* (2013.01); *A61L 2202/182* (2013.01); *A61L 2300/202* (2013.01); *A61L 2300/404* (2013.01); *A61L 2300/606* (2013.01); *A61L 2400/10* (2013.01); *A61L 2420/02* (2013.01); *A61L 2420/04* (2013.01); *A61L 2420/06* (2013.01); *A61M 11/005* (2013.01); *C10M 2229/0445* (2013.01); *C10N 2030/16* (2013.01); *C10N 2040/50* (2020.05); *C10N 2050/08* (2013.01)

(56) References Cited

U.S. PATENT DOCUMENTS

| | | | |
|---|---|---|---|
| 3,445,420 A * | 5/1969 | Kookootsedes | ........ C08L 83/04 524/862 |
| 3,490,651 A | 1/1970 | Abplanalp | |
| 3,675,821 A | 7/1972 | Morane et al. | |
| 3,775,452 A | 11/1973 | Karstedt | |
| 3,814,730 A * | 6/1974 | Karstedt | ............. C08G 77/398 528/30 |
| 4,234,108 A | 11/1980 | Diamond | |
| 4,340,155 A | 7/1982 | Obrist | |
| 4,791,149 A | 12/1988 | Pocknell | |
| 5,020,694 A | 6/1991 | Pettengill | |
| 5,026,768 A | 6/1991 | Liles | |
| 5,211,316 A | 5/1993 | Adalberto et al. | |
| 5,431,303 A | 7/1995 | Miskell | |
| 5,447,987 A | 9/1995 | Sato et al. | |
| 5,577,637 A | 11/1996 | Voss | |
| 5,647,510 A | 7/1997 | Keller | |
| 5,776,268 A | 7/1998 | Mcjames et al. | |
| 5,780,543 A | 7/1998 | Adachi et al. | |
| 6,265,480 B1 | 7/2001 | Enami et al. | |
| 6,537,246 B1 | 3/2003 | Unger et al. | |
| 6,613,185 B1 | 9/2003 | Valade et al. | |
| 6,951,654 B2 * | 10/2005 | Malcolm | ................ A61P 31/00 424/430 |
| 7,393,547 B2 * | 7/2008 | Nelson | ................... A61F 2/203 424/486 |
| 7,481,333 B2 | 1/2009 | Goldberg et al. | |
| 7,798,366 B2 | 9/2010 | Hoshino | |
| 8,021,650 B2 | 9/2011 | Tamareselvy et al. | |
| 8,357,147 B2 | 1/2013 | Burkinshaw et al. | |
| 8,596,499 B2 | 12/2013 | Vogt et al. | |
| 8,728,599 B2 | 5/2014 | Fang et al. | |
| 8,969,910 B2 | 3/2015 | Katayama | |
| 9,038,858 B2 | 5/2015 | Hanai et al. | |
| 9,180,476 B2 | 11/2015 | Werner et al. | |
| 9,302,282 B2 | 4/2016 | Bertin et al. | |
| 9,408,971 B2 | 8/2016 | Carlyon | |
| 9,422,404 B2 | 8/2016 | Curtis et al. | |
| 9,434,857 B2 | 9/2016 | Ou | |
| 9,511,034 B1 | 12/2016 | Garrett | |
| 9,642,949 B2 * | 5/2017 | Hai | ...... A61L 33/0011 |
| 9,649,650 B2 | 5/2017 | Werner et al. | |
| 9,655,917 B2 * | 5/2017 | Hai | ......... A61L 31/10 |
| 9,764,099 B2 | 9/2017 | Rimsa et al. | |
| 10,219,793 B2 | 3/2019 | Quintero et al. | |
| 10,441,947 B2 | 10/2019 | Ou | |
| 2001/0011162 A1 | 8/2001 | Epstein | |
| 2001/0019721 A1 | 9/2001 | Brandt et al. | |
| 2002/0076260 A1 | 6/2002 | Heusser | |
| 2002/0193879 A1 * | 12/2002 | Seder | ...................... A61F 2/203 623/9 |
| 2003/0044451 A1 * | 3/2003 | McGhee | ............... A61L 29/085 424/443 |
| 2003/0077316 A1 | 4/2003 | Nichols et al. | |
| 2003/0082223 A1 | 5/2003 | Healy et al. | |
| 2003/0183651 A1 | 10/2003 | Greer | |
| 2004/0004088 A1 | 1/2004 | Yerby et al. | |
| 2004/0181943 A1 * | 9/2004 | Kwiecien | ............... B26B 21/443 30/41 |
| 2005/0020844 A1 * | 1/2005 | Nelson | ................... C08G 77/04 556/467 |
| 2005/0029296 A1 | 2/2005 | Hansen et al. | |
| 2005/0048124 A1 * | 3/2005 | Sarangapani | .......... A61K 33/38 424/486 |
| 2005/0127119 A1 | 6/2005 | Keller | |
| 2005/0182443 A1 | 8/2005 | Jonn et al. | |
| 2005/0256573 A1 * | 11/2005 | Seder | ...................... A61F 2/203 623/9 |
| 2006/0009099 A1 * | 1/2006 | Jonn | ...................... A61L 15/58 442/43 |
| 2006/0134313 A1 * | 6/2006 | Guggenbichler | ........ A61L 29/06 427/2.1 |
| 2007/0043332 A1 * | 2/2007 | Malcolm | ................ A61K 9/0036 604/500 |
| 2007/0104665 A1 | 5/2007 | Jones et al. | |
| 2007/0293820 A1 | 12/2007 | Dacquay et al. | |
| 2008/0054020 A1 | 3/2008 | Pierson et al. | |
| 2008/0275403 A1 | 11/2008 | Maaskamp et al. | |
| 2009/0004246 A1 * | 1/2009 | Woolfson | ................... A61K 31/00 424/430 |
| 2009/0026660 A1 * | 1/2009 | Nelson | ................... A61L 27/54 264/331.13 |
| 2009/0076480 A1 * | 3/2009 | Pudleiner | ................ A61L 29/06 604/508 |
| 2009/0108021 A1 | 4/2009 | Hansen et al. | |
| 2010/0280547 A1 | 11/2010 | D'Alessio et al. | |
| 2010/0330025 A1 * | 12/2010 | Messersmith | .......... A61L 27/50 424/78.17 |
| 2011/0027753 A1 | 2/2011 | Maurat et al. | |
| 2011/0091669 A1 * | 4/2011 | Tang | ................ C08J 7/043 428/34.1 |
| 2011/0143148 A1 | 6/2011 | Butts et al. | |
| 2011/0272433 A1 | 11/2011 | Vogt et al. | |
| 2012/0237461 A1 | 9/2012 | Yu et al. | |
| 2012/0328787 A1 * | 12/2012 | Marrot | ................ C09D 183/04 427/387 |
| 2013/0004586 A1 * | 1/2013 | Vachon | ................... B01J 41/07 424/618 |
| 2013/0059109 A1 | 3/2013 | Kretschmann et al. | |
| 2013/0122314 A1 * | 5/2013 | Ou | ......... A61L 29/085 427/2.12 |
| 2013/0123720 A1 | 5/2013 | Lind et al. | |
| 2013/0150828 A1 * | 6/2013 | Conway | ............... A61L 29/085 604/544 |

(56) References Cited

U.S. PATENT DOCUMENTS

| | | | | |
|---|---|---|---|---|
| 2013/0171265 | A1* | 7/2013 | Saxena | A61K 8/899 424/618 |
| 2013/0310780 | A1* | 11/2013 | Phillips | A61L 15/26 604/319 |
| 2013/0310781 | A1* | 11/2013 | Phillips | C08L 83/04 604/319 |
| 2014/0221522 | A1* | 8/2014 | Antoni | A61L 31/10 523/105 |
| 2014/0277120 | A1* | 9/2014 | Cichocki | A61L 31/10 606/222 |
| 2015/0159066 | A1* | 6/2015 | Hartwell | A61M 1/90 604/319 |
| 2015/0367039 | A1* | 12/2015 | Ou | C09D 183/04 427/2.28 |
| 2016/0120706 | A1 | 5/2016 | Collinson et al. | |
| 2016/0220497 | A1* | 8/2016 | Caprasse | A61K 8/895 |
| 2016/0354172 | A1* | 12/2016 | Krogman | C08J 7/056 |
| 2017/0224823 | A1* | 8/2017 | Blanda | A61K 31/565 |
| 2018/0030327 | A1 | 2/2018 | Zhang et al. | |
| 2018/0163090 | A1* | 6/2018 | Ou | C09D 183/14 |
| 2018/0338945 | A1* | 11/2018 | Sambasivam | A61P 31/04 |
| 2019/0001019 | A1 | 1/2019 | Lindgren et al. | |
| 2020/0171198 | A1* | 6/2020 | Ou | A61L 29/16 |
| 2020/0172740 | A1* | 6/2020 | Ou | B05D 3/0493 |
| 2021/0369258 | A1 | 12/2021 | Ou et al. | |
| 2021/0369276 | A1 | 12/2021 | Ou et al. | |
| 2021/0369639 | A1 | 12/2021 | Ou | |
| 2021/0371190 | A1 | 12/2021 | Ou et al. | |
| 2021/0371596 | A1 | 12/2021 | Ou et al. | |
| 2021/0371658 | A1 | 12/2021 | Ou | |
| 2021/0371662 | A1 | 12/2021 | Ou | |

FOREIGN PATENT DOCUMENTS

| | | |
|---|---|---|
| CN | 106009688 A | 10/2016 |
| EP | 3388037 A1 | 10/2018 |
| JP | 11349897 A | 12/1999 |
| KR | 0039498 A | 4/2016 |
| WO | 9725085 A1 | 7/1997 |
| WO | 2010/128855 A2 | 11/2010 |
| WO | 2013/074732 A1 | 5/2013 |
| WO | 2016094084 A1 | 6/2016 |
| WO | 2017158340 A1 | 9/2017 |

OTHER PUBLICATIONS

International Search Report dated Aug. 13, 2021 for International Application No. PCT/IB2021/054533.
International Search Report dated Aug. 18, 2021 for International Application No. PCT/IB2021/054531.
International Search Report dated Feb. 21, 2020 for International Application No. PCT/IB2019/060233.
International Search Report dated Feb. 21, 2020 for International Application No. PCT/IB2019/060235.
International Search Report dated Jan. 11, 2022 for International Application No. PCT/IB2021/054534.
International Search Report dated Jul. 29, 2021 for International Application No. PCT/IB2021/054515.
International Search Report dated Jul. 30, 2021 for International Application No. PCT/IB2021/054518.
IP.com search of the PGPub (Year: 2021).
Lewis, et al., The chemistry of fumarate and maleate inhibitors with platinum hydrosilylation catalysts, Journal of Organometallic Chemistry, 1996, pp. 221-227, vol. 521 Issue 1.

* cited by examiner

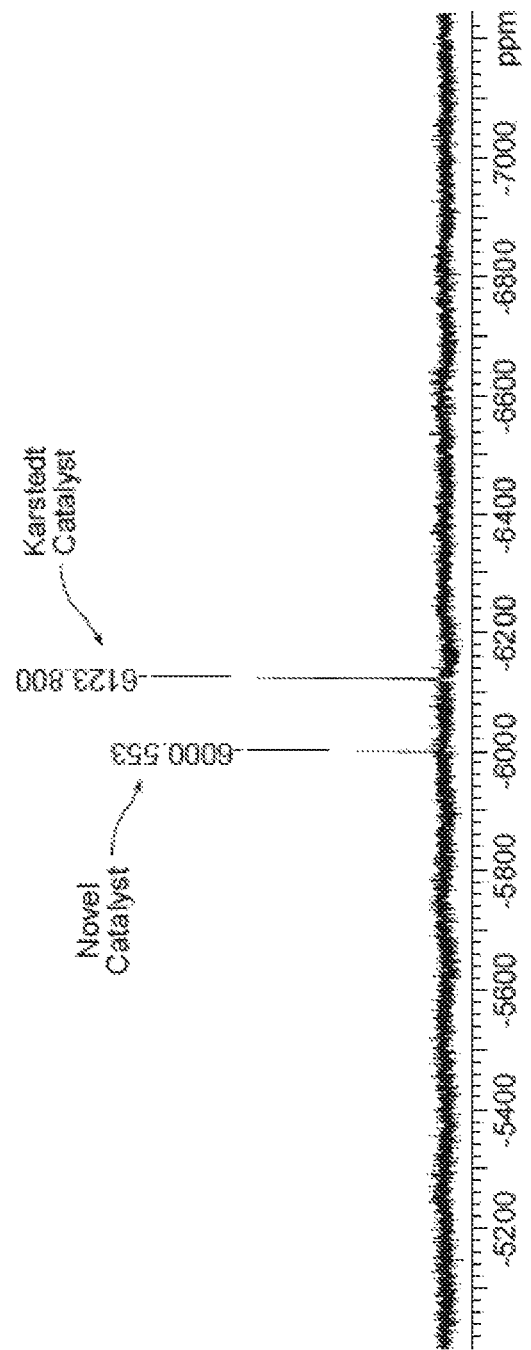

LOW TEMPERATURE CURED SILICONE LUBRICIOUS COATINGS

CROSS-REFERENCE TO RELATED APPLICATION(S)

This application claims the benefit of U.S. Provisional Application No. 62/773,102 filed Nov. 29, 2018, the contents of which is incorporated herein by reference in its entirety for all purposes.

This application is related to U.S. Non-Provisional Application No. 16/697,223, being filed concurrently herewith and having a common assignee the contents of which are herein incorporated by reference in their entirety for all purposes.

TECHNICAL FIELD

The field of art to which this invention pertains is silicone-based lubricious coatings, in particular, silicone-based lubricious coatings for use on medical devices.

BACKGROUND OF THE INVENTION

Lubricious coatings are typically required for implantable or insertable medical devices such as sutures, hypodermic needles, surgical needles, catheters, and cutting devices that contact tissue. The primary purpose of such coatings is to ease the penetration or insertion of the device into and through tissue, thereby facilitating a procedure.

A number of conventional, biocompatible lubricants have been developed for such applications, and they are typically silicone (e.g., polydimethylsiloxane) or silicone-containing coatings. For example, condensation-cured silicone coatings are known to be useful as lubricious coatings on medical devices. Such coating formulations contain amino and alkoxyl functional groups, which can be cured (cross-linked) at relatively low temperatures and high humidity levels. It is also known to use an aminopropyl-containing silicone as a lubricious coating for syringe needles. Those coatings use an epoxy-containing silicone as a cross-linking agent and may have improved penetration performance with multiple penetrations. It is also known to utilize thermoplastic polymers such as polypropylene (e.g., in powder form) in blends of silicone solutions to improve the mechanical properties of the resulting coating layers. The polypropylene powders may increase the durability of silicone needle coatings without sacrificing lubricity. Most of the known and conventionally used silicone coatings listed above require a lengthy thermal curing step after application, which is quite often unsuitable for rapid, high speed production processes.

Attempts have been made to improve coating cure times including rapid UV curable silicone lubricious coatings that can be cured rapidly (<10 seconds) on a medical device, such as needle, after UV light exposure. However, the potential hazard of certain UV curable components typically contained in such coatings may provide cause for concern.

Karstedt of GE Silicone invented a highly active platinum catalyst for hydrosilylation at the beginning of the 1970's (U.S. Pat. No. 3,775,452). The "Karstedt catalyst" is highly active at ambient temperature, and this quality makes it difficult to use in most commercial silicone coatings without the addition of an inhibitor. Several other platinum catalysts had been subsequently invented attempting to address this problem. For example, platinum-cyclovinylmethylsiloxane complex was made immediately after the invention of the Karstedt catalyst (U.S. Pat. No. 3,814,730), and this catalyst is purported to provide longer production process pot life for a vinyl/hydride reactive coating solution mixture.

Commonly assigned U.S. Pat. Nos. 9,434,857 and 10,441,947 describe novel, lubricious coatings for medical devices. The coatings provide improved lubricity and durability, and are readily applied in conventional coating processes. These patents are also directed to a novel platinum catalyst for use in such coatings. The catalyst provides for rapid curing, while inhibiting cross-linking at ambient temperatures, thereby improving the production pot life of the coatings. A limitation of such compositions is that they are not suitable for coating of polymeric materials that would be deformed due the elevated temperatures (e.g., above 160 C) required for the compositions to be cured to form coatings.

In order to be useful on medical devices such as surgical needles and sutures, it is critical that lubricious silicone coatings be durable and easy to apply in a uniform, consistent manner. A surgical procedure in which tissue is approximated or closed with surgical sutures typically requires multiple passes of the surgical needle and suture through tissue. Ease of penetration over multiple passes through tissue will make the surgeon's job easier and this will likely result in a better tissue repair or closure. The patient will benefit not only by enhanced healing and superior outcome, but also by a faster procedure resulting in a shorter time for possible exposure of the wound or opening to pathogens in the environment, and also requiring a shorter period of time that the patient is under general anesthesia, when anesthesia is required.

Some medical devices such as surgical needles are typically manufactured in high speed production processes. For example, U.S. Pat. No. 5,776,268, incorporated by reference, discloses such processes. After the needles are formed and shaped (typically from wire stock), the in-process needles are cleaned, and the needles are coated with lubricious coatings in a conventional manner such as by dipping, spraying, brushing, etc. After application of the coatings in a uniform manner to substantially coat the exterior surfaces of the needles, the needles are then moved into appropriate curing equipment, such as an oven, for a coating curing process wherein energy (e.g., thermal) is provided to cure the silicone coatings.

Silicone coatings are typically prepared at the manufacturing site by mixing the silicone polymer components with a suitable catalyst and solvents. Such coatings and catalysts, especially when of medical grade for use on medical devices, are expensive and typically have what is conventionally known in this art as a short "pot life". The term pot life, as conventionally used in the art, has the meaning that the silicone coatings when mixed with catalyst and ready for application in a coating process typically have a limited amount of time in which they are useful because of cross-linking that occurs at ambient conditions in the production facility. Such short pot life can result in a number of known problems, including for example, premature curing, leading to a viscosity increment of the coating solution during the time of its usage. This will typically cause inconsistencies in the resulting coating on the surface of the medical device, resulting in both visual and performance deficiencies.

There is a need in this art for improved silicone coatings for medical devices that have improved lubricity and durability for multiple passes through tissue. There is also a need for improved catalytic compositions and silicone coatings that have improved cure times without sacrificing lubricity and durability, which do not contain potentially harmful ingredients and are capable of being applied under conditions that do not deform the device to be coated such as sutures and other polymeric devices.

There is a further need in the art for improved catalysts for silicone coatings that provide for rapid curing when exposed to heat but which are relatively stable in a silicone coating solution over time at ambient conditions and for extended periods of time in typical production environments.

SUMMARY OF THE INVENTION

Accordingly, novel catalytic compositions and lubricious silicone coating compositions are disclosed.

In one embodiment, the coating compositions contain a first cross-linkable silicone polymer having reactive functionalities, a siloxane cross-linking agent, and a silica-containing composition with may be added as a separate component, but more preferably contained in the cross-linkable silicone polymer. The coating compositions may also contain a platinum catalyst.

Another aspect of the present invention is a medical device having a surface, wherein at least part of the surface is coated with the above-described novel silicone coating composition.

Yet another aspect of the present invention is a method of coating a medical device with a silicone, lubricious coating composition. In the novel method of coating the medical device, a medical device is provided having a surface. A lubricious silicone coating is applied to at least part of the surface. The coating composition contains a cross-linkable silicone polymer and a silica-containing composition which may be added as a separate component, but more preferably contained in the cross-linkable silicone polymer. The coating also contains a silicone cross-linking agent and a catalyst.

Still yet another aspect of the present invention is a novel platinum catalyst for use with cross-likable silicone coatings. The catalyst consists of a platinum complex having the following formula:

Pt[(CH$_2$=CH)(CH$_3$)$_2$Si]O.C$_6$H$_{10}$(OH)(C=CH)

A further aspect of the present invention is a method of curing a cross-linkable silicone polymer containing coating solution using the above-described catalyst.

These and other aspects and advantages of the present invention will become more apparent from the following description.

BREIF DESCRIPTION OF THE DRAWINGS

FIG. 1 is an NMR peak comparison of the Karstedt Catalyst compared with the NMR peak of the novel catalyst of this invention.

DETAILED DESCRIPTION OF THE INVENTION

The terms silicone and siloxane are conventionally used interchangeably in this art, and that usage has been adopted herein. Furthermore, as used herein, the term "ambient temperature(s)" is intended to describe temperatures from about 20 to about 25 C.

Lubricious Coating Compositions

One aspect of the present invention is directed to novel lubricious silicone coating compositions which are particularly useful for coating surfaces of medical devices such as surgical needles and sutures and other polymeric medical devices.

In one embodiment, the compositions include a mixture of a cross-linkable siloxane polymer and a silica-containing composition which may be added as a separate component, but more preferably contained in the cross-linkable silicone polymer, a conventional silicone cross-linking agent, and a platinum catalyst. The silicone polymer components are blended with conventional aromatic organic solvents, including, for example, xylene and aliphatic organic solvents (such as, for example, hexane, heptane or its commercial derivatives) to form coating solutions or compositions. Other solvent suitable for coating solution includes and not limited to low molecular weight siloxane, e.g., hexamethyldisiloxane.

The cross-linkable siloxane polymers useful in the coating compositions of the present invention will have reactive functionalities or terminal functional groups, including but not limited to vinyl terminated, hydroxyl and acrylate functional groups. The cross-linkable siloxane polymers that can be used in the lubricious coatings of the present invention preferably include vinyl terminated polydialkylsiloxane or vinyl terminated polyalkyarylsiloxane. Examples include but are not limited to the following vinyl terminated siloxane polymers: polydimethyl siloxane, polydiphenylsilane-dimethylsiloxane copolymer, polyphenylmethylsiloxane, polyfluoropropylmethyl-dimethylsiloxane copolymer and polydiethylsiloxane. It is particularly preferred to use vinyl terminated cross-linkable polymethyl siloxane.

The cross-linking agents that can be used in the coatings of the present invention include conventional silicone cross-linking agents such as, for example, polymethylhydro siloxane, polymethylhydro-co-polydimethylsiloxane, polyethyhydrosiloxane, polymethylhydrosiloxane-co-octylmethylsiloxane, polymethylhydrosiloxane-co-methylphenylsiloxane. One preferred conventional catalyst for use in the coatings of the present invention is polymethylhydro siloxane. Precise control of cross-link density in the coatings of the present invention is achieved by precise control of the ratio of non-cross-linkable silicone polymer (e.g., polydimethylsiloxane) to fully cross-linked polymer. The fully cross-linked polymer is formed by a reaction between the functionalized cross-linkable polymer and the cross-linking agent, for example, a vinylsilylation reaction between vinyl-terminated polydimethylsiloxane and polymethylhydrosiloxane optionally in the presence of a platinum complex catalyst. The ratio between non-cross-linkable polymer, e.g., polydimethylsiloxane, and fully cross-linked polymer is sufficiently effective to provide structural reinforcement to the resulting interpenetrating polymer networks, and is typically between about 0.1 wt./wt. and about 9 wt./wt., preferably between about 0.40 wt./wt. and about 4.0 wt./wt. (weight of cross linker against weight of vinyl terminated polydimethylsiloxane) The vinyl-terminated cross-linkable base polymer, e.g., polydimethylsiloxane base polymer, useful in the coatings of the present invention will have a molecular weight of from about 9000 and about 400,000 and preferably from about 40,000 to about 100,000. Examples of this polymer include but are not limited to: Gelest Product Code No. DMS-V31, DMS-V33, DMS V-35, DMS V42, DMS-V46, DMS-V52, etc., available from Gelest, Inc., Morrisville, Pa. 19067. The typical molecular structure of vinyl terminated polymethyldisiloxane is the following:

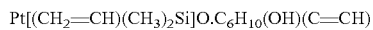

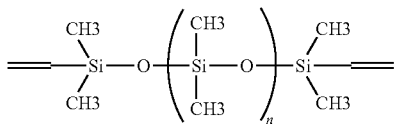

wherein n is defined by the molecular weight.

The molecular weights of the silicone polymers used wherein can be estimated based on the relationship between viscosity and molecular weight (page 11, SILICONE FLUIDS: STABLE, INERT MEDIA ENGINEERING AND DESIGN PROPERTIES, Catalog published by Gelest, Inc. 11 East Steel Rd. Morrisville, Pa. 19067). Using A. J. Barry's relationship for molecular weights (M)>2,500 correlating the kinematic viscosity µ expressed in centistokes (cSt) at 25 C, the molecular weight M of silicones can be estimated as follows:

$$\log \mu_{cSt} = 1.00 + 0.0123 M^{0.5}$$

(as published by A. J. Barry in the Journal of Applied Physics 17, 1020 (1946))

The cross-linkable siloxane polymer forms the matrix phase of the coating on surface or surfaces of a medical device. Vinyl terminated polydimethylsiloxane reacts with polymethylhydrosiloxane cross-linker in the presence of platinum catalyst under appropriate conditions; the vinyl terminated polydimethylsiloxane linear polymers are fully cross-linked to each other as the result of this reaction. The amount of polymethylhydrosiloxane cross-linker is in large stoichiometric excess compared to vinyl terminated polydimethylsiloxane base polymer. It is believed that the extra SiH functions in the cross-linker react with the OH functions on the surface of the medical devices, e.g., polymeric sutures, to form Si—O—C bonds at elevated temperature or in the case of steel needles, to form Si—O—Fe bonds. Covalent bonds thus created between the silicone coating and the device, as the result of this reaction, result in the adhesive attachment of the coating to the device's surface.

The polymethyhydrosiloxane cross-linkers, or cross-linking agents, used in the practice of the present invention will have a molecular weight between about 1000 and about 3000, and preferably between about 1400 and about 2100. An example of this polymer cross-linker includes, but is not limited to, Gelest Product Code No. HMS-991, HMS-992, available from Gelest, Inc., Morrisville, Pa. 19607. The typical molecular structure of the polymethylhydrosiloxane cross-linker is the following:

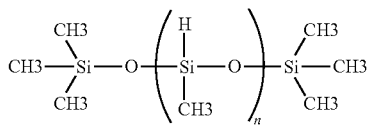

wherein n is defined by the molecular weight.

Polymethylhydro-co-polydimethylsiloxane can also be used as cross-linker or cross-linking agent in the novel coatings of the present invention. Examples of this polymer include, but are not limited to, Gelest Product Code No. HMS-301, HMS-501. The molecular weight of this siloxane polymer cross-linking agent will typically be between about 900 and about 5,000, and preferably about 1,200 to about 3,000. The typical molecular structure of polymethylhydro-co-polydimethylsiloxane cross linker is the following:

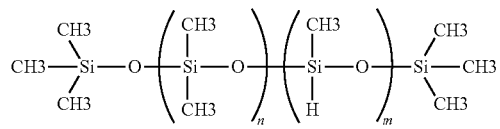

wherein n and m are defined by the molecular weight.

Silica-Containing Compositions

As used herein, the silica-containing compositions described for use with this invention include silica materials as a separate component (such as surface treated silica) or from commercially available compositions that contain silica in a cross linkable silicone polymer mixture.

As a separate component, silica is incorporated into the coatings of this invention to improve its mechanical properties and create some form of friction to ensure knot security for the suture. Hexamethyl silyl surface treatment is needed for the silica filler to enable its compatibility to the polysiloxane polymer matrix which prevents phase separation in the coating solution. An example of treated silica includes hexamethyldisilazane treated silica i.e., trimethyl silyl surface treated silica filler (Gelest SIS6962.0).

In the case of silicone polymers already containing silica, these may be obtained from commercially available sources such as silica-containing composition selected from reactive silica-containing silicone bases including HCR (high consistent rubber) bases and LSR (liquid silicone rubber) bases, preferred are LSR bases. Other commercial examples of this material include and is not limited to Wacker 401-10, 401-20, 401-40 base; and a liquid silicone rubber base, a commercial example of this material includes and is not limited to Bluestar Silbione LSR 4370 base. These type of commercial silicone rubber bases are prepared by mixing a surface-treated silica filler with various molecular weights of vinyl terminated polydimethylsiloxane polymer. In-situ surface treatment may be performed during the mixing process to improve the compatibility between filler and polysiloxane polymer.

Catalyst

Bruce Karstedt of GE Silicone invented a highly active platinum catalyst (the "Karstedt catalyst") at the beginning of the 1970's (U.S. Pat. No. 3,775,452). Vinyl-terminated polydimethylsiloxane can react with a polymethylhydrosiloxane cross-linker in less than one minute at ambient temperature with as little as 10 ppm of the Karstedt catalyst. It is typically difficult or impossible to use this catalyst in conventional needle and suture manufacturing processes because of its high rate of catalytic activity, and since the economics of conventional production processes ideally. Typically require up to a one week pot life for the fully catalyzed silicone coating solution for needle coating process and one shift (8 hr) pot life for suture coating process. The novel fast curing platinum catalyst of the present invention has been developed to address this issue, and the resulting mixtures of this novel catalyst together with the cross-linkable silicone polymers of the present invention, e.g., vinyl-terminated polydimethylsiloxane and polymethylhydrosiloxane, with silica fillers can be stable at ambient temperatures for 8 hours. The cross-linking reaction between the crosslinkable silicone polymer and the cross-linking agent, for example, vinyl-terminated polydimethylsiloxane and polymethylhydrosiloxane, in the presence of the novel catalyst of the present invention can be switched on in less than 30 seconds at moderate elevated temperature (i.e., 70-110 C). The novel catalyst of the present invention is prepared by reacting the Karstedt catalyst with vinylcyclohexanol according to Scheme 1 as seen below. The novel catalyst of the present invention provides greater control over curing of the silicone coating solutions. This is conventionally referred to as "command cure".

Scheme 1

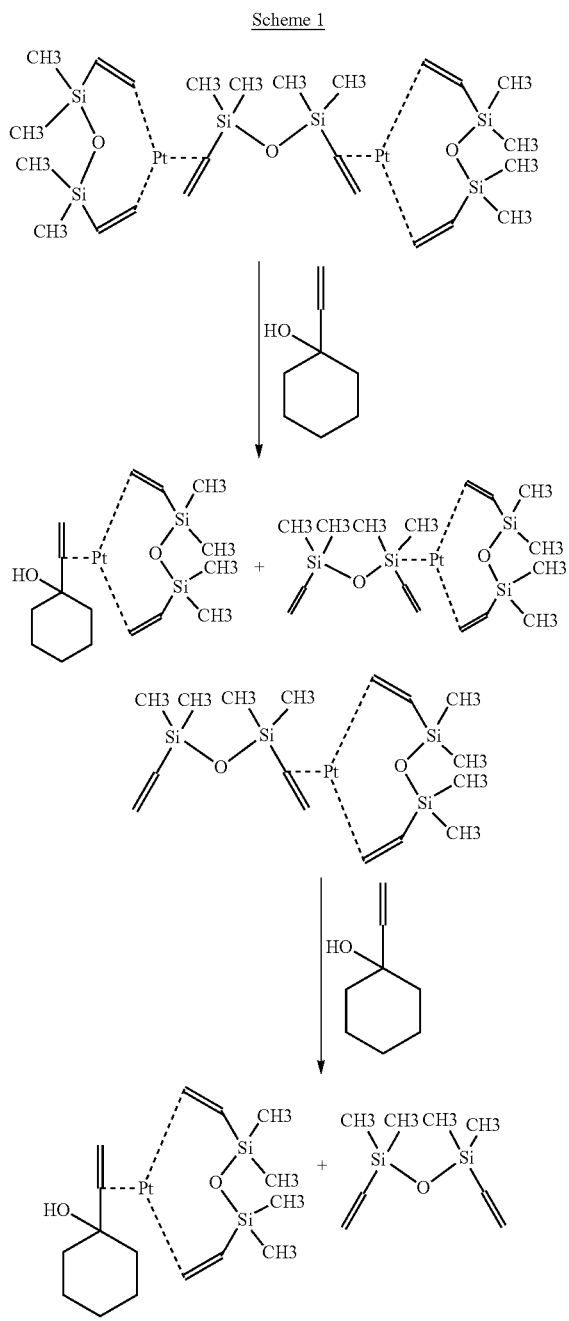

The novel catalyst of the present invention may be prepared in the following manner. Karstedt catalyst in xylene solution is mixed with a low concentration of vinylcyclohexanol in a xylene solution at ambient temperature for a sufficiently effective time to complete the reaction, e.g., a half an hour, and completion of the reaction is indicated by a change of the color of the reaction mixture, from clear to light brown.

The resulting catalyst solution containing the novel catalyst of the present invention is ready to use in the preparation of the lubricious coating solutions of the present invention. The formula of the resulting platinum complex catalyst (platinum divinyltetramethyldisiloxane complex) is:

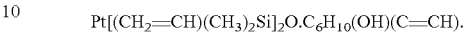

It should be noted that the resulting catalyst reaction mixture will contain a small amount of the reaction product divinyltetramethyldisiloxane. This component does not affect the catalyst and is a low boiling point component that is rapidly boiled off. Accordingly, purification of the catalyst mixture to remove divinyltetramethyldisiloxane is optional, and it is believed that its presence will not affect the cross-linking reaction of a cross-linkable silicone polymer. The novel catalyst of the present invention is inhibited at low or ambient temperatures and activated at higher or curing temperatures, that is, the catalyst is inactivated at lower or ambient temperatures and activated at higher or curing temperatures. This allows for command cure (command cure catalytic action) of the cross-linkable components in silicone coatings to rapidly form coating films at desired curing temperatures and provides for long pot life and suitable for suture coating processes.

Solvent and Coating Mixing Procedure

The above silicone polymers and novel platinum catalyst are dispersed into low boiling point organic solvents to form the lubricious coating solution. Low temperature aliphatic solvents are used for the silicone dispersion. Aromatic solvents and hexamethyldisiloxane are commonly used for silicone dispersion. Typical examples include, but are not limited to, pentane, heptanes, hexane and their mixtures. The organic solvents are added at a concentration sufficient to allow effective blending of the silicone polymer components into a homogeneous coating solution. The total solvent concentration is from about 80 wt. % to about 99 wt. %, and is and is more typically from about 85 wt. % to about 93 wt. %, depending upon the coating thickness requirement. Those skilled in the art will appreciate that the coating thickness can be engineered by changing the solids content of the coating solution.

The sequence of the addition of components is important. The typical coating composition is prepared in the following manner. In the case when the silica is added as a separate component, the vinyl terminated polydimethylsiloxane is dispersed into the first solution such as hexamethyldisiloxane together with surface treated silica for up to two hours until fully homogeneous (solution 2). Heptane is then added (solution 3) and further mixing for one hour prior to the addition of polymethylhydrosiloxane cross linker. The solution is fully blended for one more hour after all of the catalyst is added as the final component In the following paragraph, the wt. % is the wt. % of total solid content in the coating solution. The novel coating compositions of the present invention will contain sufficient amounts of the polymeric components, silica-containing composition, cross-linking agent, catalyst, and solvent to effectively provide a silicone coating having high lubricity and durability, a long pot life, and suitable for application in conventional coating processes using conventional coating equipment.

Typically, the amount of the silica in the coating solution will be about 5 wt. % to about 40 wt. % (total solids), more typically about 10 wt. % to about 30 wt. % (total solids), and preferably about 15 wt. % to about 25 wt. % (total solids). The amount of the cross-linkable silicone polymer will typically be about 60 wt. % to about 95 wt. % (total solids), more typically about 70 wt. % to about 90 wt. % (total solids), and preferably about 75 wt. % to about 85 wt. % (total solids). The amount of the silicone cross-linking agent will typically be about 0.2 wt. % to about 6 wt. % (total solids), more typically about 1 wt. % to about 5 wt. % (total solids), and preferably about 2 wt. % to about 4 wt. % (total solids). The amount of the platinum catalyst based upon the total solids in the novel lubricious silicone coating compositions (platinum element in total solids) of the present invention will typically be about 0.0004 wt. % to about 0.0036 wt. %, more typically about 0.0012 wt. % to about 0.0028 wt. %, and preferably about 0.0016 wt. % to about 0.0024 wt. %.

The amount of organic solvent in the coating compositions of the present invention will typically be about 75 wt. % to about 99.5 wt. %, more typically about 80 wt. % to about 95 wt. %, and preferably about 85 wt. % to about 93 wt. %. Those skilled in the art will appreciate that the amount of solvent present in the novel coating compositions of the present invention will vary with several factors, and that the solvent quantity in the coating compositions will be selected to engineer an efficacious coating. The factors typically considered include the method of application, the method of cure, the coating equipment utilized, ambient conditions, thickness, etc. It will be appreciated that each of the components of the coating compositions of the present invention may consist of blends of those components. For example, two or more different molecular weight non-cross-linkable silicone polymers may be used, or two or more cross-linkable silicone polymers having different functionalities and/or molecular weights may be used, etc.

Coating Process

The novel silicone lubricious coating solution of the present invention is applied to the surface of a medical device such as a polyester suture using conventional coating techniques and processes and conventional coating equipment. An example of coating equipment can be simple dip coating tanks and in-line convection oven for curing the coating. The coating can also be applied by a brushing, rolling, or spraying process. The vinyl silylation addition cross linking reaction can be completed in-line by passing through a drying oven. The curing time can be as short as 20 seconds at 100 C, 120 seconds at 95 C or 60 minutes at 70 C. Flash cure can be achieved with the present lubricious silicone coating.

Due to the deformable nature of the polymeric medical devices at elevated temperatures, it is desirable to not exceed treatment or coating temperatures above 120 C in the practice of this invention. Preferred coating treatment temperatures range from about 60-110 C, more preferably from about 90-100 C, and most preferably about 95 C.

Other conventional curing techniques which can be utilized with the novel silicone coating compositions of the present invention include thermal (e.g., convection heating), ultraviolet light, plasma, microwave radiation, electromagnetic coupling, ionizing radiation, laser, and the like. Prior to coating, the surfaces of the medical devices will be prepared in a conventional manner using conventional processes such as electro-polishing, oxidation, ultrasonic cleaning, plasma, corona discharge treatment, chemical cleaning, and the like.

Test Procedures for Coating Performance

Coating performance for medical devices coated with the novel compositions of the present invention can be tested with a variety of conventional friction or adhesion tests. In the case of surgical sutures, coating performance, durability and integrity may be evaluated using the following tests.

Ease of Passage Test

To evaluate the force of friction to pull a suture through tissue, a simple comparative test was used. The intent of the test was not to quantify an absolute number for the force of passage but to establish a comparison between suture samples.

A block of high density (approximatively 210 Kg/m3 or 13PCF) polyurethane foam, 25 millimeters thick, was used as a substrate. A one-eyed needle was used to pull the suture through the thickness of the foam. The end of the suture was attached to a load cell and placed in a tensile tester to measure the maximum force to pull the suture. The displacement speed was set at 2 inches per minute.

Knot Security Test

The knot security test consists of evaluating the behavior of a knot when the suture is under tension. The test is conducted in a tensile tester at constant displacement. The suture is immersed in sodium chloride isotonic solution for 24 hours and tested wet. The knot is rated as being secured (no slippage), slip and break, or slip through (no break). The maximum pull force can also be reported.

As mentioned previously above, the medical devices that may be coated with the novel lubricious coatings include conventional medical devices such as surgical needles and sutures, hypodermic needles, catheters, surgical probes, endoscopes, syringes, scalpels, cutting blades, orthopaedic implants, trocars, cannulas, and the like. The medical devices will be constructed from conventional biocompatible materials including surgical stainless steels, PTFE, glass, alloyed steels, refractory metal alloys, memory alloys, polymers, composites comprising metallic and non-metallic components ingredients, combinations thereof, and the like. The biocompatible materials may include nonabsorbable materials and bioaborbable materials.

The following examples are illustrative of the principles and practice of the present invention, although not limited thereto:

EXAMPLE 1

Platinum Catalyst (Synthesis Procedure)

6 g of Gelest SIP 6831 (2.2% platinum divinyl tetramethyldisiloxane complex in xylene, Karstedt catalyst) was mixed with 6 g of vinylcyclohexanol for 30 minutes at ambient temperature and the mixture turns into light brown color. 2 g of the mixture was submitted for $^{195}$Pt NMR measurement. The rest of the mixture was further mixed for 5 hours until dark brown. 10 g of the mixture was diluted with 990 g of tetramethyldisiloxane for further usage in the later examples.

The evidence of the formation of the new Pt catalyst according to scheme 1 rest mainly on its $^{195}$Pt NMR spectroscopic identification. Karstedt catalyst give a distinguishable peak at approximately −6124 ppm. A new peak for the novel catalyst at approximately −6001 ppm is formed 30 minutes into the mixing process as illustrated in FIG. 1.

EXAMPLE 2a

Preparation of Suture Coating Solution 5.7 g of commercial high durometer silica-containing liquid silicone base rubber (Bluestar Silbione LSR4370base) were mixed with 0.17 g polyhydromethylsiloxane cross linker (Gelest HMS 991) and two solvents (11.4 g hexamethyldisiloxane and 60.6 g heptane) for 1 hour prior to addition of 1.0 g of the catalyst of Example 1. The final mixture was stirred for 30 minutes at ambient temperature.

EXAMPLE 2b

Coating of Size 2-0 Polyester Suture 1 meter of polyester suture (Ethicon 2-0 Mersilene) was immersed into the coating solution of Example 2a for 5 seconds and cured at a temperature of 100 C for 5 minutes.

EXAMPLE 2c

Coating of Size 1 Polyester Suture 50 meters of polyester suture (Ethicon 1 Mersilene) was immersed into coating solution of Example 2a for 2 seconds and cured in an in-line curing oven at a temperature of 95 C for 2 minutes.

EXAMPLE 3a

Preparation of Suture Coating Solution 2.85 g of commercial high durometer silica-containing liquid silicone base rubber (Bluestar Silbione LSR4370base) were mixed with 0.085 g polyhydromethylsiloxane cross linker (Gelest HMS 991) and two solvents (11.4 g hexamethyldisiloxane and 63.5 g heptane) for 1 hour prior to addition of 0.5 g of the catalyst of Example 1. The final mixture was stirred for 30 minutes at ambient temperature.

EXAMPLE 3b

Coating of 2-0 Polyester Suture 1 meter of polyester suture (Ethicon 2-0 Mersilene) was immersed into the coating solution of Example 3a for 5 seconds and cured at a temperature of 100 C for 5 minutes.

EXAMPLE 4a

Preparation of Suture Coating Solution 5.7 g of commercial high durometer silica-containing liquid silicone base rubber (Bluestar Silbione LSR4370base) were mixed with 0.17 g polyhydromethylsiloxane cross linker (Gelst HMS 991) and two solvents (11.4 g hexamethyldisiloxane and 23 g heptane) for 1 hour prior to addition of 1.0 g of the catalyst of Example 1. The final mixture was stirred for 30 minutes at ambient temperature.

EXAMPLE 4b

Coating of Size 2-0 Polyester Suture 1 meter of polyester suture (Ethicon 2-0 Mersilene) was immersed into the coating solution of Example 3a for 5 seconds and cured at a temperature of 100 C for 5 minutes.

EXAMPLE 4c

Coating of Size 1 Polyester Suture 50 meters of polyester suture (Ethicon size 1 Mersilene) was immersed into coating solution of Example 4a for 2 seconds and cured in an in-line curing oven at a temperature of 95 C for 2 minutes.

CONTROL EXAMPLE 1a (Silica-Free Coating) Preparation of Suture Coating Solution 9.5 g of Gelest XG2385B (a mixture of vinyl terminated polydimethyl siloxane and cross linker polymethylhydrosiloxane) was mixed with 0.55 g of the composition of Example 1 and 30.5 g heptane for 1 hour.

CONTROL EXAMPLE 2a

Identical Composition to Example 2a, but Uses Karstedt Catalyst Instead for Pot Life Measurement 5.7 g of commercial high durometer silica-containing liquid silicone base rubber (Bluestar Silbione LSR4370base) were mixed with 0.17 g polyhydromethylsiloxane cross linker (Gelest HMS 991) and two solvents (11.4 g hexamethyldisiloxane and 60.6 g heptane) for 1 hour prior to addition of 1.0 g of the 1.0% Gelest SIP 6831 (2.2% platinum divinyl tetramethyldisiloxane complex (Karstedt) in xylene) in xylene. The final mixture was stirred for 1 minutes at ambient temperature.

CONTROL EXAMPLE 1b

Coating of 2-0 Polyester Suture 1 meter of polyester suture (Ethicon 2-0 Mersilene® suture) was immersed into the coating solution of Control Example 1a for 5 seconds and cured at a temperature of 100 C for 5 minutes.

CONTROL EXAMPLE 1c

Coating of Size 1 Polyester Suture 50 meters of polyester suture (Ethicon size 1 Mersilene) was immersed into the coating solution of Example 1a for 2 seconds and cured in an in-line curing oven at a temperature of 95 C for 2 minutes.

Performance Testing

1. Suture Passage Testing

Size 2-0 Polyester Suture

Suture passage testing was performed on Examples 2b and 3b, Control Example 1, Uncoated Suture and two commercial coated sutures (Ethibond® suture and Ti-Cron™ suture). Dimensions of all the sutures are the same (2-0) and the results are summarized in Table 1.

TABLE 1

Size 2-0 Polyester Suture Passage Testing

| Sample | Wet Force (g) | Dry Force (g) |
|---|---|---|
| Example 2b | 37.8 | 26.4 |
| Example 3b | 45.3 | 47.5 |
| Control Example 1b | 17.5 | 20.5 |
| Commercial Sample 1 (Ethibond ® Suture) | 81.7 | 56.4 |
| Commercial Sample 2 (Ti-Cron ™ Suture) | 77.1 | 60.8 |
| Uncoated Sample (Mersilene ® Suture) | 97.1 | 56.4 |

Size 1 Polyester Suture

Suture passage testing was performed on Examples 2c and 4c, Control Example 1c, Uncoated Suture and one commercial coated suture (Ethibond® suture). Dimensions of all the sutures are the same (Size 1) and the results are summarized in Table 2.

TABLE 2

Size 1 Polyester Suture Passage Testing

| Sample | Dry Force (g) |
|---|---|
| Example 2c | 63.2 |
| Example 4c | 58.0 |
| Control Example 1c | 54.3 |
| Commercial Sample 1c (Size 1 Ethibond Suture) | 100.4 |
| Uncoated Sample (Size 1 Mersilene Suture) | 136.0 |

Referring to Table 1, one observes that substantially less force was required for size 2-0 polyester suture example 2b and Control Example 1 (silica-free) to pass through the test media, compared to an uncoated suture and conventional coated suture (Ethibond®, Tri-Cron™) which shows that the silicone coatings of the present invention show its intended effect of lowering the force needed to pass the coated sutures through the polyurethane foam versus the commercial sutures. The observation is consistent in Size 1 suture testing referring to Table 2. Both inventive examples and control samples give substantially lower passage force than the commercial product.

2. Knot Security Testing

Knot security testing was performed on Examples 2b, 3b and 4b, Control Example 1, uncoated suture and two commercial coated sutures (Ethibond® suture and Ti-Cron™ suture). Dimensions of all the sutures are the same (2-0) and the results are summarized in Table 3.

TABLE 3

Size 2-0 Suture Knot Security Testing

| Sample | Maximum Load (lb.) | Knot Security Occurrence (%) |
|---|---|---|
| Example 2b | 14.5 | 33 |
| Example 3b | 8.2 | 0 |
| Example 4b | 16.0 | 95 |

TABLE 3-continued

Size 2-0 Suture Knot Security Testing

| Sample | Maximum Load (lb.) | Knot Security Occurrence (%) |
|---|---|---|
| Control Example 1b | 1.0 | 0 |
| Commercial Sample 1 (Ethibond) | 16.4 | 30 |
| Commercial Sample 2 (Ti-Cron) | 15.2 | 90 |
| Uncoated Sample (Mersilene) | 17.5 | 100 |

Knot security testing was performed on Examples 2c, 4c, and one commercial coated suture (Ethibond® suture). Dimensions of all the sutures are the same (Size 1) and the results are summarized in Table 4.

TABLE 4

Size 1 Polyester Suture Knot Security Testing

| Sample | Maximum Load (lb.) | Knot Security Occurrence (%) |
|---|---|---|
| Example 2c | 38.4 | 90 |
| Example 4c | 38.0 | 100 |
| Commercial Sample (Size 1 Ethibond) | 26.3 | 50 |
| Control example 1c | 1.8 | 0 |

Referring to Table 3, one observes quite surprisingly that the knot security performance of Example 2b is comparable to commercial coated polyester suture (Ethibond®), while the conventional silicone coated suture (Control Example 1) lost all of the knot security.

Referring to Table 4, both inventive examples give better knot security performance than the commercial coated polyester suture (Ethibond)

3. Pot Life

A pot life study was conducted for Examples 2a, 3a and 4a, together with Control Examples 1a and 2a, by observing changes in viscosity of the solution. The viscosities of these samples were measured over a period of 8 hours and the results are summarized in Table 5.

TABLE 5

Viscosity Changes in Coating Solutions Over Time (cPs)

| Sample | 5 min | 1 hr | 4 hr | 8 hr |
|---|---|---|---|---|
| Example 2a | 2.00 | 2.25 | 2.00 | 2.25 |
| Example 3a | 1.50 | 1.50 | 1.50 | 3.00 |
| Example 4a | 7.25 | 7.00 | 7.50 | 7.25 |
| Control Example 1a | 7.50 | 7.25 | 7.50 | 7.75 |
| Control Example 2a | 3.50 | Gel* | | |

*sample ceases to flow after 25 minutes.

Example 2a, 3a, 4a and Control Example 1a (which all containing the novel catalyst of this invention) gives consistent viscosities for up to 8 hours, which is suitable for the typical suture coating production cycle. The Karstedt catalyst (Control Example 2a) is unable to provide consistent viscosity and gels within 25 minutes, which renders it unsuitable for any meaningful scale suture coating process.

The novel coatings and catalyst of the present invention have many advantages compared with the coatings and catalysts of the prior art. The coatings allow for precise control over the cross-linked polymer network structure, leading to consistency of the resulting coatings and the consistency of the performance of coated devices, in particular coated surgical sutures. The coatings provide a unique polymeric network structure, which provides both lubricity and durability of the resulting silicone coating. The catalyst provides command cured catalytic action, enabling the coating solution to form a film rapidly while possessing desirably long pot life. The catalyst is inhibited at low or ambient temperatures and uninhibited or reactivated at temperatures that do not deform polymeric sutures or other polymeric medical devices. The coatings and catalysts provide for more efficient coating and curing processes.

Although this invention has been shown and described with respect to detailed embodiments thereof, it will be understood by those skilled in the art that various changes in form and detail thereof may be made without departing from the spirit and scope of the claimed invention.

We claim:

1. A medical device coated with a lubricious silicone coating, comprising:
   a medical device having a surface; and,
   a lubricious silicone coating on at least a part of the surface, the coating formed from a coating composition comprising:
   a cross-linkable silicone polymer having reactive functionalities;
   a silica-containing composition;
   a silicone cross-linking agent; and,
   a catalyst, wherein said catalyst is an ambient inactive catalyst and consists essentially of platinum divinyltetramethyldisiloxane vinylcyclohexanol complex having the formula:

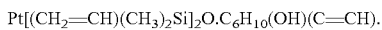
   Pt[(CH$_2$=CH)(CH$_3$)$_2$Si]$_2$O.C$_6$H$_{10}$(OH)(C=CH).

2. The medical device of claim 1, wherein the cross-linkable silicone polymer is selected from the group consisting of vinyl terminated polydialkylsiloxane, vinyl terminated polydimethylsiloxane, vinyl terminated polydiphenylsilane-dimethylsiloxane copolymer, vinyl terminated polyphenylmethylsiloxane, vinyl terminated polyfluoropropylmethyl-dimethylsiloxane copolymer and vinyl terminated polydiethylsiloxane.

3. The medical device of claim 1, wherein the cross-linkable silicone polymer comprises vinyl terminated polydimethylsiloxane.

4. The medical device of claim 1, wherein the silica-containing composition comprises a trimethyl silyl surface treated silica filler.

5. The medical device of claim 1, wherein the silica-containing composition is selected from the commercially available reactive silica-containing silicone bases including HCR (high consistent rubber) bases and LSR (liquid silicone rubber) bases.

6. The medical device of claim 5, wherein the silica-containing composition is a liquid silicone rubber base.

7. The medical device of claim 1, wherein the silicone cross-linking agent is selected from the group consisting of polymethylhydrosiloxane, polymethylhydro-co-polydimethylsiloxane, polyethylhydrosiloxane, polymethylhydrosiloxane-co-octylmethylsiloxane, and polymethylhydrosiloxane-co-methylphenylsiloxane.

8. The medical device of claim 1, wherein the silicone cross-linking agent comprises polymethylhydrosiloxane.

9. The medical device of claim 1, wherein the coating composition additionally comprises about 75 wt. % to about 93 wt. % of an organic solvent, based upon the weight of the coating composition.

10. The medical device of claim 1, wherein the coating composition comprises about 0.2 wt. % to about 6 wt. % of the silicone cross-linking agent based on total solids, wherein the coating composition additionally comprises about 75 wt. % to about 93 wt. % of an organic solvent, based upon the weight of the coating composition.

11. The medical device of claim 1, wherein the coating composition comprises about 0.0004 wt. % to about 0.0036 wt. % of the platinum catalyst, based on total solids, wherein the coating composition additionally comprises about 75 wt. % to about 99.5 wt. % of an organic solvent, based upon the weight of the coating composition.

12. The medical device of claim 1, wherein the coating composition additionally comprises a solvent selected from the group consisting of xylene, toluene, pentane, hexane, heptanes, octane, mixtures of higher molecular weight olefins, and combinations thereof.

13. The medical device of claim 1, wherein the medical device comprises a biocompatible material selected from the group consisting of stainless steels, PTFE, glasses, ceramics, polymers, refractory metal alloys, memory alloys, and composites of metals and non-metals.

14. The medical device of claim 1, wherein the medical device is selected from the group consisting of surgical needles, sutures, hypodermic needles, surgical scalpels, catheters, cutting blades, surgical probes, endoscopes, scissors, and cutting blades.

15. The medical device of claim 14, wherein the medical device comprises a surgical suture.

* * * * *